United States Patent [19]

Seng et al.

[11] 4,150,022

[45] Apr. 17, 1979

[54] PROCESS FOR THE PRODUCTION OF AMMONIUM SALTS OF DITHIOCARBAMIC ACID

[75] Inventors: Florin Seng, Schildgen; Kurt Ley, Odenthal-Gloebusch, both of Fed. Rep. of Germany

[73] Assignee: Bayer Aktiengesellschaft, Leverkusen, Fed. Rep. of Germany

[21] Appl. No.: 833,629

[22] Filed: Sep. 15, 1977

Related U.S. Application Data

[63] Continuation of Ser. No. 572,789, Apr. 29, 1975, abandoned.

[30] Foreign Application Priority Data

May 11, 1974 [DE] Fed. Rep. of Germany ....... 2422955

[51] Int. Cl.$^2$ ........................................... C07D 211/96

[52] U.S. Cl. ........................ 260/239 BF; 260/326.83; 260/501.12; 544/58; 544/85; 544/357; 546/189

[58] Field of Search ......... 260/268 S, 501.12, 239 BF, 260/326.83; 544/357

[56] References Cited

U.S. PATENT DOCUMENTS

3,607,870  9/1971  Becke et al. ...................... 260/268 S

Primary Examiner—Paul M. Coughlan, Jr.
Attorney, Agent, or Firm—Sprung, Felfe, Horn, Lynch & Kramer

[57] ABSTRACT

This invention relates to a new process for the production of ammonium salts of dithiocarbamic acid; the process comprising reacting bis-alkyl aminomethanes with sulphur.

8 Claims, No Drawings

PROCESS FOR THE PRODUCTION OF AMMONIUM SALTS OF DITHIOCARBAMIC ACID

This is a continuation, of application Ser. No. 572,789, filed Apr. 29, 1975, now abandoned.

This invention relates to a new process for the production of ammonium salts of dithiocarbamic acid, the process comprising reacting bis-dialkyl aminomethanes with sulphur.

It has been found that ammonium salts of dithiocarbamic acid corresponding to the general formula (I):

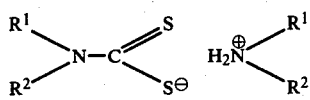

in which $R^1$ and $R^2$, which may be the same or different, each represents an optionally substituted aliphatic radical, in addition to which $R^1$ and $R^2$, together with the nitrogen atom substituted by them, may form a 5-membered to 7-membered heterocyclic ring, can be obtained by reacting bis-dialkyl aminomethanes corresponding to the general formula (II):

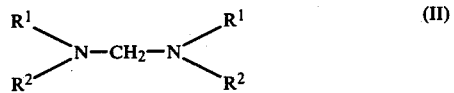

in which $R^1$ and $R^2$ are as defined above, with sulphur.

The reaction is generally carried out at temperatures in the range of from 0° C. to 100° C., preferably at tempertures in the range of from 50° C. to 100° C. and more especially at temperatures in the range of from 80° C. to 100° C.

Optionally substituted aliphatic radicals are linear or branched alkyl radicals with up to 18 carbon atoms, preferably with up to 12 carbon atoms and more especially with up to 6 carbon atoms, such as for example methyl, ethyl, propyl, isopropyl, n-butyl, isobutyl, tert.-butyl, amyl, isoamyl, also the isomers, hexyl, heptyl, octyl, nonyl, decyl, undecyl, dodecyl and higher radicals, such as myristyl, palmityl, cetyl and stearyl.

The heterocyclic 5- to 7-membered rings, which the radicals $R^1$ and $R^2$ can form together with the nitrogen atom substituted by them, may also contain further hetero atoms such as oxygen, sulphur or nitrogen, and may even be substituted. Examples of these heterocyclic rings are pyrrolidine, piperidine, hexamethylene imine, morpholine, thiamorpholine and piperazine.

Substituents by which the aforementioned radicals may be substituted include any groups and radicals which are inert to sulphur under the conditions of the process according to the invention, the following being mentioned by way of example: the nitro and cyano groups, alkyl and aryl radicals, and also alkoxy and dialkyl amino groups, the alkyl radicals in the aforementioned groups having the scope of meaning indicated above.

Aryl radicals are those with up to 14 carbon atoms, preferably phenyl and naphthyl.

Bis-dialkyl aminomethanes corresponding to the formula (II), which may be used as starting compounds in the process according to the invention, are known or may be obtained by known methods (L. Henry, B1 [3] 13, 157 (1895) ).

The following bis-dialkyl aminomethanes, for example, may be used in the process according to the invention: bis-dimethyl aminomethane, bis-diethyl aminomethane, bis-di-n-propyl aminomethane, bis-pyrrolidinomethane, bis-piperidinomethane, bis-morpholinomethane and bis-hexamethylene iminomethane.

In general, sulphur is used in a quantity of at least 2 mols per mol of the bis-dialkyl aminomethane, although it is also possible to use an excess or deficit of sulphur.

In general, the reaction according to the invention is carried out in an organic or aqueous medium.

The process according to the invention may be carried out as follows:

The bis-dialkyl aminomethane used is dissolved and/or suspended with sulphur in an organic solvent or water, followed by heating until the reaction is finished. The end of the reaction may be detected from the disappearance of the sulphur and, in cases where a non-aqueous solvent is used, from the precipitation of the water-soluble dithiocarbamic acid ammonium salts. In general, the reaction is over after about 2 to about 15 hours. The dithiocarbamic acid ammonium salts formed are then isolated in the usual way by filtration, precipitation by the addition of a solvent in which the end products are insoluble, or by concentrating the solution by evaporation.

Organic solvents suitable for use in the process according to the invention are lower aliphatic alcohols such as methanol, ethanol, propanol, isopropanol and tert.-butanol, nitriles such as acetonitrile, propionitrile, adipic acid dinitrile and benzonitrile, formamides such as dimethyl formamide, and also pyridine and quinoline.

The reaction is illustrated by the following equation which relates by way of example to the reaction of bis-piperidinomethane:

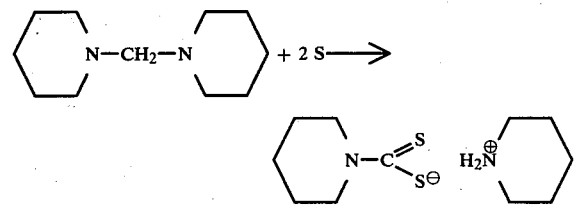

Ammonium salts of dithiocarbamic acid are important intermediate products for the production of tetraalkyl thiuram disulphides. These disulphides are known vulcanisation accelerators and plant protection agents (Houben-Weyl, Methoden der Organischen Cehmie, Vol. IX, page 853). Until now the ammonium salts of the dithiocarbamic acids have been prepared by reacting carbon disulphide with amines. In comparison to this known process the process according to the invention has the essential advantage that in it is used sulphur as starting material instead of carbon disulphide which can be handled only under special precautions because of its high inflammability and toxicity.

The ammonium salts of the dithiocarbamic acids, e.g. dimethyl amine salt of N,N-dimethyl-dithiocarbamic acid, are transformed by oxydation, e.g. with sodium hypochlorite, to the tetraalkyl thiuram disulphides, e.g. tetramethyl thiuram disulphide.

EXAMPLE 1

A mixture of 18.2 g (0.1 mol) of bis-piperidinomethane and 6.4 g (0.2 mol) of sulphur is heated for 10 hours to boiling point in 30 ml of acetonitrile. The brown product formed is filtered off under suction, giving 20 g (81% of the theoretical) of piperidine N,N-pentamethylene dithiocarbamate which melts at 163° C. to 167° C. after dissolution in and crystallisation from methanol.

Analysis: $C_{11}H_{22}H_2S_2$ (mol 246). Calculated: C 53.7 H 8.9 N 11.4. Found: C 53.7 H 9.0 N 11.6.

EXAMPLE 2

A mixture of 30.8 g (0.2 mol) of bis-pyrrolidinomethane and 12.8 g (0.4 mole) of sulphur is heated for 5 hours to boiling point in 50 ml of ethanol. The yellow product formed is filtered off under suction, yielding 22.4 g (82% of the theoretical) of pyrrolidine N,N-tetramethylene dithiocarbamate which melts at 153° C.–155° C. after dissolution in and crystallisation from ethanol.

EXAMPLE 3

A mixture of 17.6 g (0.1 mol) of bis-morpholinomethane and 6.4 g (0.2 mol) of sulphur is heated for 11 hours to 85° C. in 25 ml of dimethyl formamide and 25 ml of ethanol. The pale yellow product formed is filtered off under suction, yielding 18 g (75% of the theoretical) of morpholine N,N-(3-oxapentyl)-dithiocarbamate which melts at 192° C.–195° C. after dissolution in and crystallisation from ethanol/water.

EXAMPLE 4

A mixture of 12.2 g (0.12 mol) of bis-dimethyl aminomethane and 6.4 g (0.2 mol) of sulphur is introduced into 30 ml of dimethyl formamide, followed by stirring for 5.5 hours at approximately 80° C. After cooling and the addition of 100 ml of ether, dimethylamine N,N-dimethyl dithiocarbamate melting at 128° C. is obtained in a yield of 11.5 g (71% of the theoretical).

Analysis: $C_5H_{14}N_2S_2$ (mol 166). Calculated: C 36.2 H 8.4 N 16.9. Found: C 35.9 H 8.5 N 16.8.

We claim:

1. A process for the production of an ammonium salt of a dithiocarbamic acid corresponding to the general formula

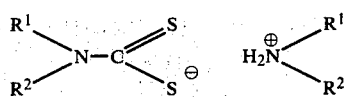

in which $R^1$ and $R^2$, which may be the same or different and each represents, an unsubstituted alkyl radical having up to 18 carbon atoms or a substituted alkyl radical having up to 18 carbon atoms where the substituent is a nitro group, a cyano group, phenyl or naphthyl, an alkoxy radical where the alkyl group derived contains up to 12 carbon atoms, or a dialkyl amino group where the alkyl groups each contain up to 12 carbon atoms, or $R^1$ and $R^2$ when taken together may form a 5-membered to 7-membered heterocyclic ring selected from the group consisting of pyrrolidine, piperidine, hexamethyleneimine, morpholine, thiamorpholine and piperazine which may be substituted by a nitro group, a cyano group, an alkyl group with up to 12 carbon atoms, phenyl or naphthyl, an alkoxy group whose alkyl group contains up to 12 carbon atoms, or a dialkylamino group where the alkyl components thereof contain up to 12 carbon atoms, which consists essentially of reacting sulfur with a bisaminomethane corresponding to the formula

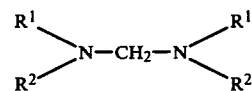

in which $R^1$ and $R^2$ are as defined above.

2. A process according to claim 1, where $R^1$ and $R^2$ are taken together to form a 5-membered to 7-membered heterocyclic ring and said heterocyclic ring is a hexamethyleneimine ring.

3. A process according to claim 1 wherein $R^1$ and $R^2$ are taken together to form a 5-membered to 7-membered heterocyclic ring selected from the group consisting of pyrrolidine, piperidine, hexamethyleneimine, morpholine, thiamorpholine and piperazine.

4. A process according to claim 1 wherein the reaction is carried out at a temperature in the range of from 0° to 100° C.

5. A process according to claim 1 wherein the temperature is 50° to 100° C.

6. A process according to claim 1 wherein the temperature is from 80° to 100° C.

7. A process according to claim 1 wherein the reaction is carried out in an organic or aqueous medium.

8. A process according to claim 1 wherein sulfur is used in a quantity of at least 2 mols per mol of the bisamino methane.

* * * * *